United States Patent [19]

Bodor

[11] 4,094,983
[45] June 13, 1978

[54] METHOD FOR REDUCING INTRAOCULAR PRESSURE IN WARM-BLOODED ANIMALS

[75] Inventor: Nicholas S. Bodor, Lawrence, Kans.

[73] Assignee: Interx Research Corporation, Lawrence, Kans.

[21] Appl. No.: 759,779

[22] Filed: Jan. 17, 1977

[51] Int. Cl.² .................. A61K 31/455; A01N 9/24
[52] U.S. Cl. ............................. 424/266; 424/311; 424/312
[58] Field of Search .................. 424/266, 311, 312

[56] References Cited

U.S. PATENT DOCUMENTS

| | | | |
|---|---|---|---|
| 3,657,244 | 4/1972 | Mentrup et al. | 424/311 |
| 3,809,714 | 5/1974 | Hussain et al. | 424/311 |
| 3,839,584 | 10/1974 | Hussain et al. | 424/311 |
| 3,922,348 | 11/1975 | Seidehamel et al. | 424/330 |
| 3,937,838 | 2/1976 | Wetterlin et al. | 424/311 |
| 3,959,485 | 5/1976 | Windheuser | 424/311 |
| 4,031,242 | 6/1977 | Jones et al. | 424/311 |

Primary Examiner—Albert T. Meyers
Assistant Examiner—D. W. Robinson
Attorney, Agent, or Firm—Bacon & Thomas

[57] ABSTRACT

Intraocular pressure in warm-blooded animals is reduced by topically applying to the eye thereof, an effective ophthalmologically acceptable amount of a compound of the formula:

Formula I

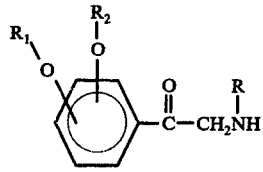

wherein R represents a member selected from the group consisting of hydrogen or a $C_1$–$C_5$ straight or branched alkyl group; and wherein $R_1$ and $R_2$, which may be the same or different, represents an acyl member selected from the group consisting of alkanoyl having 1–22 carbon atoms, alkenoyl having one or two double bonds and having 4–22 carbon atoms,

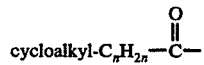

having a total of 4–10 carbon atoms of which 3–7 are ring carbon atoms in cycloalkyl and wherein $n$ is zero, one, or two, phenoxyacetyl, naphthalenecarbonyl, pyridinecarbonyl,

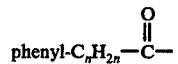

wherein $n$ is zero, one or two and phenyl is unsubstituted or is substituted by 1–3 alkyl having 1–4 carbon atoms, alkoxy having 1–4 carbon atoms, halo, trifluoromethyl, dialkylamino having 2–8 carbon atoms, and alkanoylamino having 1–6 carbon atoms; or an ophthalmologically acceptable acid addition salt thereof.

21 Claims, No Drawings

METHOD FOR REDUCING INTRAOCULAR PRESSURE IN WARM-BLOODED ANIMALS

BACKGROUND OF THE INVENTION

1. Field of the Invention

The present invention is directed to a method for reducing intraocular pressure in warm-blooded animals. More specifically, the present invention is directed to reducing intraocular pressure in warm-blooded animals through the use of a select group of "keto" sympathomimetic amines.

2. Description of the Prior Art

Ocular hypertension is associated with glaucoma, a disease of the eye characterized by a progressive increase in intraocular pressure which occurs over a prolonged period of time and which, if untreated, continues until the optic nerve is deteriorated to such an extent that blindness occurs. The goal in the treatment of glaucoma is to reduce the intraocular pressure sufficiently to prevent damage to the optic nerve. The adrenergic amine, epinephrine, when applied topically to the eye, is a widely used treatment for glaucoma. Miotics, which include certain parasympathomimetics such as pilocarpine and cholinesterase inhibitors such as physostigmine, are also widely employed topically. However, due to the increase in side effects observed with existing drugs, their partial application in the treatment of glaucoma is questionnable. For instance, common undesirable side effects induced by the miotic drugs include twitching of the eyelids, browache, headache, extensive ocular pain, conjunctival congestion, etc. Localized allergy occasionally develops as well. Absorption of the topically applied drug occasionally causes systemic effects also. This is particularly true with the cholinesterase inhibitors which may cause salivation, sweating, nausea, vomiting, bradycardia, hypotension, etc., and with adrenergic (sympathomimetic) agents which may cause tachycardia, hypertension, headaches, sweating, tremors, etc. The alpha-adrenergic stimulating action of epinephrine, for instance, frequently causes mydriasis and sometimes, retinal maculophehy during prolonged usage.

Isoproterenol, an adrenergic agent, whose action differs from epinephrine in that it is considered almost exclusively a beta-adrenergic stimulator, has been evaluated by Ross and Drance, *Arch. Ophthal.*, 83, 39–43 (1970), in patients suffering from ocular hypertension. Satisfactory reduction in intraocular pressure as a result of ocular installation of a 5% isoproterenol hydrochloride solution was obtained. However, concomitant side effects of a serious nature were also observed which prohibited the continued practical use of this drug in the treatment of glaucoma. Among side effects associated with the administration of isoproterenol for reduction of intraocular pressure were marked and dangerous tachycardia of up to 100–150 beats per minute as well as palpitations, a nervous feeling, and weakness.

A clinical study designed to determine the effect of diverse sympathomimetic agents on ocular tension has also been reported by R. Weekers, et al., *American Journal of Ophthamology*, 40, 666–672 (1955). Included in the study were such diverse sympathomimetic amines as adrenalone (the corresponding ketone derivative of adrenalin) and the dextrorotatory (d) and levorotatory (l) optical isomers of adrenalin (epinephrine). The study established that l-adrenalin (a strong sympathomimetic agent) lowered ocular tension, whereas the corresponding ketone derivative, adrenalone and d-adrenalin (agents having only minimal sympathomimetic activity) do not. As a result of these findings, R. Weekers, et al. concluded that reduced ocular tension results from sympathetic stimulation.

In addition to the foregoing, U.S. Pat. Nos. 3,809,714, 3,839,584 and 3,868,461 and 3,959,485, owned by the present assignee of record, all disclose the use of chemically modified sympathomimetic amines in the treatment of glaucoma and other ailments receptive to sympathomimetic amine activity. Specifically, the dipivaloxy derivatives of epinephrine and isoproterenol are disclosed.

U.S. Pat. No. 3,922,348 discloses successful treatment of intraocular hypertension (glaucoma) with a compound designated as 3,4-dihydroxy-2-(isopropylamino) acetophenone, the corresponding ketone derivative of isoproterenol. A review of this reference reveals that the patentee employs rather excessive concentrations (3%) of the active compound to achieve reduction of intraocular pressure. See, Table I. Additionally, this compound is highly unstable and thus limited in terms of shelf-life.

SUMMARY OF THE INVENTION

The present invention relates to a method for lowering intraocular pressure in warm-blooded animals. More particularly, the present invention concerns itself with a method for lowering intraocular pressure in warm-blooded animals, and particularly, the mammalian eye, which comprises topically administering thereto, an effective (but minimal) ophthalmologically amount for lowering intraocular pressure of a compound selected from the group consisting of:

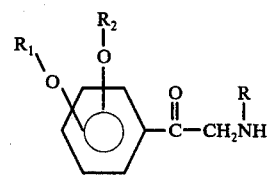

wherein R represents a member selected from the group consisting of hydrogen or a $C_5$–$C_5$ straight or branched alkyl group; and wherein $R_1$ and $R_2$, which may be the same or different, represents an acyl member selected from the group consisting of alkanoyl having 1–22 carbon atoms, alkenoyl having one or two double bonds and having 4–22 carbon atoms, cycloalkyl-$C_nH_{2n}$—C— having a total of 4–10 carbon atoms of which 3–7 are ring carbon atoms in cycloalkyl and wherein $n$ is zero, one or two, phenoxyacetyl, naphthalenecarbonyl, pyridinecarbonyl, phenyl-$C_nH_{2n}$—C— wherein $n$ is zero, one or two and phenyl is unsubstituted or is substituted by 1–3 alkyl having 1–4 carbon atoms, alkoxy having 1–4 carbon atoms, halo, trifluoromethyl, dialkylamino having 2–8 carbon atoms and alkanoylamino having 1–6 carbon atoms; or an ophthalmologically acceptable acid addition salt thereof.

The compounds of the type encompassed by Formula I such as 3,4-bis(pivalyloxy)phenyl-methylaminomethylketone perchlorate and 3,4-bis(pivalyloxy)phenyl-isopropylaminomethylketone perchlorate have heretofore only been known to be useful as intermediates in the preparation of therapeutically active compounds disclosed as claimed in U.S. Pat. Nos. 3,809,714, 3,839,584 and 3,868,461 previously noted.

By simply choosing the appropriate α-halo-3,4-dihydroxyacetophenone and the appropriate R and $R_1$ moieties, all free amino ketone compounds of Formula I can be prepared in accordance with the synthesis scheme disclosed in the above-identified '714, '584 and '461 patents vis-a-vis 3,4-bis(pivalyloxy)phenyl-methylaminomethylketone perchlorate and 3,4-bis(pivalyloxy)phenyl-isopropylaminomethylketone (pivalyloxy) perchlorate, respectively. The perchlorate acid-addition salt is obtained via the method described in U.S. Pat. No. 3,809,714. All other acid-addition salts are prepared by first isolating the perchlorate salt. Next the perchlorate salt is reacted with a stoichiometric amount of a suitable base such as NaOH, KOH, Ca(OH)$_2$ or NH$_4$OH to obtain the free amino ketone derivative. Finally, the free base derivative is reacted with an excess of the chosen ophthalmologically acceptable HX acid (wherein "X" represents an ophthalmologically acceptable acid-addition salt anion as later described) to thus obtain the corresponding ophthalmologically acceptable acid-addition salt. This procedure is standard and well-known to those skilled in the art of pharmaceutical research. The "chloride" salt can also be obtained in the manner described in pending patent application "Novel Synthesis for Preparing the Hydrochloride Salt of Selected Catecholamines", Ser. No. 703,943, filed July 9, 1976, owned by the present assignee of record. The subject matter of the above-identified references is encorporated herein by reference.

DETAILED DESCRIPTION OF THE INVENTION

When $R_1$ and/or $R_2$ in Formula I is alkanoyl containing 1-22 carbon atoms, there are included both unbranched and branced alkenoyl, for example, formyl, acetyl, propionyl, butyryl, isobutyryl, valeryl, isovaleryl, 2-methylbutanoyl, pivalyl, 3-methylpentanoyl, 3,3-dimethylbutanoyl, 2,2-dimethylpentanoyl, doco-sanoyl, and 7,7-dimethyloctanoyl. The branched alkanoyl groups are preferred over the unbranched alkanoyl groups.

When $R_1$ and/or $R_2$ in Formula I is alkenoyl having one or two double bonds and having 4-22 carbon atoms, there are included, for example, crotonyl, 9-octadecenoyl, 2,5-hexadienoyl, 3,6-octadienoyl, 10,13-octadecadienoyl, and 5,13-docosadienoyl.

When $R_1$ and/or $R_2$ in Formula I is

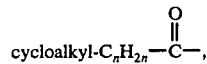

there are included for example the cycloalkanecarbonyl and cycloalkanealkanoyl groups: cyclopropanecarbonyl, 1-methylcyclopropanecarbonyl, cyclopropaneacetyl, alpha-methylcyclopropaneacetyl, 1-methylcyclopropaneacetyl, 2-amylcyclopropaneacetyl, cyclopropanepropionyl, alpha-methylcyclopropanepropionyl, 2-isobutylcyclopropanepropionyl, 2-hexylcyclopropanecarbonyl, cyclobutanepropionyl, 2-methylcyclobutanecarbonyl, 1,3-dimethylcyclobutanecarbonyl, 3,3-dimethylcyclobutanecarbonyl, cyclobutaneacetyl, 2,2-dimethyl-3-ethylcyclobutaneacetyl, cyclobutanepropionyl, cyclopentanecarbonyl, 1-methyl-3-isopropyl, cyclopentanecarbonyl, cyclopentanepropionyl, cyclohexanecarbonyl, cyclohexaneacetyl, 4-methylcyclohexaneacetyl, cycloheptanecarbonyl, 4-methylcycloheptaneacetyl, and cycloheptanepropionyl.

When $R_1$ and/or $R_2$ in Formula I is (Phenyl or substituted

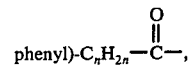

there are included for example benzoyl, phenylacetyl, alpha-phenylpropionyl, beta-phenylpropionyl, p-toluyl, m-toluyl, o-toluyl, o-ethylbenzoyo, p-tert-butylbenzoyl, 3,4-dimethylbenzoyl, 2-methyl-4-ethylbenzoyl, 2,4,6-trimethylbenzoyl, m-methylphenylacetyl, p-isobutylphenylacetyl, beta-(p-ethylphenyl)-propionyl, p-anisoyl, m-anisoyl, o-anisoyl, m-isopropxybenzoyl, p-n-butoxybenzoyl, 3-methoxy-4-ethoxybenzoyl, 3,4,5-trimethoxybenzoyl, 2,4,6-triethoxybenzoyl, p-methoxyphenylacetyl, m-isobutoxyphenylacetyl, 3,4-diethoxyphenylacetyl, beta-(3,4,5-trimethoxyphenyl) o-iodobenzoyl, m-bromobenzoyl, p-chlorobenzoyl, p-flourobenzoyl, 2-bromo4-chlorobenzoyl, 2,4,6-trichlorobenzoyl, p-chlorophenylacetyl, alpha-(m-bromophenyl)-propionyl, p-trifluoromethylbenzoyl, 2,4-di-(trifluoromethyl)-benzoyl, m-trifluoromethylphenylacetyl, beta-(p-trifluoromethyl-phenyl) propionyl, 2-methyl-4-methoxybenzoyl, 3-chloro4-ethoxybenzoyl, beta-(3-methyl-4-chlorophenyl) propionyl, p-dimethylaminobenzoyl, m-diethylaminobenzoyl, p-dibutylaminobenzoyl, p-(N-methyl-N-ethylamino) benzoyl, 0-acetamidobenzoyl, m-propionamidobenzoyl, p-hexanoylaminobenzoyl, 3-chloro-4-acetamidophenylacetyl, and p-acetamidophenylpropionyl.

When $R_1$ and/or $R_2$ in Formula I is napthhalenecarbonyl, there are included 1-naphthalenecarbonyl and 2-naphthalenecarbonyl.

When $R_1$ and/or $R_2$ in Formula I is pyridinecarbonyl, there are included picolinoyl (2-pyridinecarbonyl), nicotinoyl (3-pyridinecarbonyl), and isonicotinoyl (4-pyridinecarbonyl), and the opthalmologically acceptable acid-addition salts thereof.

While all of the compounds within Formula I suffice for the purposes of this application, a preferred group of compounds having exceptional activity at minimal concentration exists as noted below:

(1) 3,4-bis(pivalyloxy)phenyl-methylamionomethyl-ketone hydrochloride
(2) 3,4-bis(P-toluyloxy)phenyl-methylaminomethyl-ketone hydrochloride
(3) 3,4-bis(hexanoyloxy)phenyl-methylaminomethyl-ketone hydrochloride
(4) 3,4-bis(nicotinoyloxy)phenyl-methylaminomethyl-ketone hydrochloride
(5) 3,4-bis(phenylacetyloxy)phenyl-methylaminomethyl-ketone hydrochloride
(6) 3,4-bis(pivalyloxy)phenyl-aminomethyl-ketone hydrochloride
(7) 3,4-bis(p-toluyloxy)phenyl-aminomethyl-ketone hydrochloride
(8) 3,4-bis(hexanoyloxy)phenyl-aminomethyl-ketone hydrochloride
(9) 3,4-bis(nicotinoyloxy)phenyl-aminomethyl-ketone hydrochloride
(10) 3,4-bis(phenylacetyloxy)phenyl-aminomethyl-ketone hydrochloride
(11) 3,4-bis(pivalyloxy)phenyl-isopropylaminomethyl-ketone hydrochloride
(12') 3,4-bis(p-touluyloxy)phenyl-isopropylaminomethyl-ketone hydrochloride

(13) 3,4-bis(hexanoyloxy)phenyl-isopropylaminomethyl-ketone hydrochloride
(14) 3,4-bis(nicotinoyloxy)phenyl-isopropylaminomethyl-ketone hydrochloride
(15) 3,4-bis(phenylacetyloxy)phenyl-isopropylaminomethyl-ketone hydrochloride Other aspects of this invention include practicing the method of the invention with a pharmaceutically acceptable ophthalmological carrier as well as typical and coventional polymeric inserts or soft contact lenses.

Topical administration of a compound of Formula I to the eye of a warm-blooded animal effectively lowers intraocular pressure without the concomitant appearance of any significant undesirable side effects associated with the prior art.

In accordance with the present invention, the compound of Formula I or an ophthalmologically acceptable acid addition salt thereof is applied topically to the eye in an effective opthalmologically acceptable amount, thereby providing a therapeutic useful reduction in intraocular pressure. It is to be understood that the term "effective ophthalmologically acceptable amount" as used herein generally refers to the quantity of the active ingredient necessary to effect a lowering of intraocular pressure without causing any concomitant side effects associated with the prior art as heretofore described. While the administered dose, whether a single dose or a daily dose, will, of course, vary with the individual treated, the dose administered is not subject to definite bounds. However, generally, the dose administered will usually be an effective amount, or the equivalent on a molar basis of the pharmacologically active form produced upon the metabolic release of the active drug to achieve its desired pharmacological and physiological effect, i.e., a lowering of intraocular pressure. Normally, however, a dose of from 50 to 100 μl of a solution contaning from 0.01 to 2% once every 6 to 12 hours will suffice to reduce intraocular pressure.

The term "ophthalmologically acceptable acid addition salts" as used herein in describing the salts of the compound of Formula I is intended to define those salts which are nontoxic and nonirritating on topical application to the eye, stable when stored, and otherwise generally acceptable for ophthalmic formulation. By way of example, there can be mentioned those salts derived from organic or inorganic acids which are nonirritating to the ophthalmic membrane such as hydrochloric, hydrobromic, sulfuric, phosphoric, methanesulfonic, acetic, citric, malic, succinic, lactic, tartaric, benzoic and the like.

When the compound of Formula I is administered topically to the eye of a warm-blooded animal, it is preferred to maintain the same in an aqueous isotonic vehicle such as a 0.9% sodium chloride solution. Normally, one to four drops of such solution is sufficient for reducing intraocular pressure. Naturally, other vehicles and additional active ingredients may be included, provided they do not hinder the therapeutic activity of the main active drug, the compound of Formula I.

In practicing the method of the present invention, ophthalmologically acceptable acid addition salts of the compound of Formula I which are exceptionally water soluble, such as the tartrate, bitartrate, sulfate or hydrochloride salts are preferred.

Without further elaboration, it is believed that one of ordinary skill in the art can, using the preceding description, utilize the present invention to its fullest extent. Consequently, the following specific embodiments are, therefore, to be construed as merely illustrative, and not limitative, of the remainder of the specification and claims in any way whatsoever.

EXAMPLE I

INTRAOCULAR PRESSURE EVALUATION USING 3,4-BIS(PIVALYLOXY)PHENYLMETHYLAMINOMETHYL KETONE HYDROCHLORIDE (DPA)

Preparation of m,p-DIPIVALYLADRENALONE HYDROCHLORIDE (DPA):

To a methanol solution containing 44.7 g (0.099 mol) m,p-dipivalyladrenalone hydroperchlorate at 0° was added dropwise with stirring a methanol solution containing 16.7 g (0.099 mol) cesium chloride. After stirring for 0.5 hr. at 0°, the cesium perchlorate was removed by filtration and the methanol filtrate was concentrated under reduced pressure to a light yellow solid. Recrystallization of isopropanol gave 23.1 g (0.060 mol), 60%, m,p-dipivalyladrenalone hydrochloride, mp 201°–203°, tlc (silica gel/chloroform:methanol:formic acid:30:10:1 (VIV)) Rf=0.65; uv (methanol): λmax 254 nm, λ280 nm(sh); ir (KBr) 2980, 2770, 1750, 1685, 1260, 1100 and 840 cm$^{-1}$; pmr (CD$_3$COCD$_3$·D$_2$O) δ 6.8–7.7 (m, 3H), 4.4(s,2H), 2.5 (s, 3H) and 0.9 (s, 18H) ppm.

Anal. Calcd for C$_{19}$H$_{28}$ClNO$_5$: C, 59.13; H, 7.31; N, 3.63; Cs, trace. Found: C, 59.19; H, 7.22; N, 3.76; Cs, 99 PPM.

INTRAOCULAR PRESSURE STUDIES:

METHODS AND MATERIALS

Normal New Zealand albino rabbits of either sex, weighing about 2 kg. were used in the studies. The animals were placed in wooden restraining boxes at least a half hour before the experiment and remained there throughout the test. The intraocular pressure was estimated using a standard tonometer, and the pupil diameter was measured with starrett micrometer held at constant distance from observer and animal eyes. Prior to each pneuamtonometry the eye was given one drop of proparacaine HCl, (Alcaine®), 0.5% diluted 1:1 with normal saline, which was washed out a few seconds later with normal saline.

The compound was dissolved in distilled water. DPA was freely soluble. The solutions were prepared freshly just before the experiment. A dose volume of 0.05 ml from an Eppendorf pipet was used.

The results of all intraocular pressure and mydriatic studies conducted are shown below in Tables I and II.

TABLE I

| THE EFFECT OF DPA ON INTRAOCULAR PRESSURE IN NORMAL ALBINO RABBITS | | | | | | | | |
|---|---|---|---|---|---|---|---|---|
| CONCENTRATION | TIME (HOURS) | | | | | | | |
| | 0 | 1 | 2 | 4 | 6 | 8 | 10 | 23 |
| | Intraocular Pressure mmHg (X ± S.E.) | | | | | | | |
| 0% | 24.8 | 25.2 | 24.2 | 24.8 | 24.7 | 24.8 | 25.2 | 26.2 |

TABLE I-continued

THE EFFECT OF DPA ON INTRAOCULAR
PRESSURE IN NORMAL ALBINO RABBITS

| CONCENTRATION | TIME (HOURS) | | | | | | | |
|---|---|---|---|---|---|---|---|---|
| | 0 | 1 | 2 | 4 | 6 | 8 | 10 | 23 |
| | Intraocular Pressure mmHg (X ± S.E.) | | | | | | | |
| | ±0.8 | ±1.0 | ±1.2 | ±1.0 | ±1.4 | ±1.2 | ±0.7 | ±0.7 |
| 0.01% | 26.2 | 22.8 | 17.7 | 20.5 | 20.7 | 22.7 | 22.2 | 27.2 |
| | ±0.9 | ±2.1 | ±1.8 | ±2.1 | ±2.2 | ±1.8 | ±1.1 | ±0.4 |
| 0.1% | 25.2 | 24.7 | 18.7 | 16.5 | 15.2 | 16.8 | 19.3 | 25.5 |
| | ±0.9 | ±1.3 | ±1.8 | ±1.0 | ±1.6 | ±0.7 | ±0.9 | ±0.8 |
| 0.5% | 25.2 | 22.7 | 22.5 | 17.8 | 13.5 | 13.0 | 15.7 | 25.2 |
| | ±0.6 | ±1.1 | ±1.4 | ±2.3 | ±1.1 | ±0.9 | ±0.8 | ±0.8 |
| 1% | 24.3 | 21.8 | 23.8 | 18.3 | 14.5 | 14.8 | 13.2 | 22.2 |
| | ±1.1 | ±1.1 | ±1.0 | ±1.7 | ±0.4 | ±1.0 | ±0.6 | ±1.3 |

TABLE II

THE EFFECT OF DPA ON PUPIL
DIAMETER IN NORMAL ALBINO RABBITS

| CONCENTRATION | TIME (HOURS) | | | | |
|---|---|---|---|---|---|
| | 0 | 0.5 | 1.5 | 3 | 5 |
| | Pupil Diameter mm (X ± S.E.) | | | | |
| 0% | 5.0 | 5.1 | 5.0 | 5.0 | 5.0 |
| | ±0.1 | ±0.2 | ±0.1 | ±0.2 | ±0.1 |
| 0.01% | 4.7 | 5.6 | 5.2 | 4.7 | 4.7 |
| | ±0.1 | ±0.3 | ±0.2 | ±0.1 | ±0.1 |
| 0.1% | 4.8 | 6.9 | 6.7 | 5.1 | 4.7 |
| | ±0.1 | ±0.2 | ±0.2 | ±0.1 | ±0.1 |
| 0.5% | 5.0 | 7.2 | 6.9 | 5.2 | 5.0 |
| | ±0.1 | ±0.5 | ±0.3 | ±0.2 | ±0.1 |
| 1% | 5.0 | 6.6 | 6.1 | 5.0 | 4.8 |
| | ±0.1 | ±0.2 | ±0.1 | ±0.1 | ±0.1 |

When the preceding example is repeated, but this time, employing any one of the remaining compounds encompassed within Formula I, substantially similar results will be observed.

Pharameceutical compositions comprising any of the compounds of Formula I in combination with a non-toxic pharmaceutically acceptable ophthalmological carrier therefor, suitable for ocular installation, is preferred for practicing the present invention. These include opthalmic solutions, ointments or any other equivalent ophthalmic vehicles. Aqueous opthalmic solutions formulated in accordance with good pharmaceutical practices as set forth in Chapter 83 of REMINGTON'S PHARMACEUTICAL SCIENCES, Fourteenth Edition, Mac Publishing Company, are preferred, although petrolatum based ointments may suffice. The ophthalmic solutions are naturally sterilized and preferably contain a bacteriological preservative to maintain sterility during storage and use. The quaternary ammonium bacteriostats such as benzalkonium chloride are satisfactory. Antioxidants can also be employed if desirable, but in view of the fact that the compounds of Formula I are highly stable toward degradation, antioxidants will seldom be necessary. By way of example, suitable antioxidants include sodium bisulfite, N-acetylcystene salts, sodium ascorbate and other water soluble opthalmologically acceptable antioxidants known in the pharmaceutical arts.

Ophthalmic solutions of any of the compounds of Formula I may be adjusted with inert ingredients such as sodium chloride or boric acid to provide a solution which is comfortable for application to the eye. That is, adding ingredients to the basic opthalmological formulation for the purpose of achieving isotonicity with the eye are within the purview of the instant invention.

Ointments are prepared with conventional petralatum vehicles employing liquid petrolatum and white petrolatum in such proportions as to afford an ointment of desirable fluidity.

The compounds of Formula I and any opthalmological acceptable acid addition salt thereof may also be applied to the eye through the vehicle of a polymeric insert or soft contact lens. For the latter purpose, the polymeric hydrophilic hydrogels prepared from polymers of acrylic and methacrylic esters, modified collagens, cross-linked polyether gels, cross-linked polyvinyl alcohol, or cross-linked partially hydrolyzed polyvinylacetate as disclosed in U.S. Pat. Nos. 2,976,576; 3,220,960 and 3,419,006 may be employed. Ocular inserts prepared from these or other polymeric materials which are insoluble in tear fluid but which may absorb tear fluid to form a swollen hydrogel as disclosed in U.S. Pat. Nos. 3,416,530, 3,618,604 and 3,632,200 may also be employed. All such means of applying the compounds of Formula I or any ophthalmologically pharmaceutically acceptable acid addition salt thereof are included within the present invention as are compositions adapted for such use.

In practicing the process of the present invention for lowering intraocular pressure, an opthalmologically acceptable polymeric ocular insert placed and retained in contact with an eyeball is preferred wherein the compound of Formula I diffuses from the insert at a rate sufficient to provide an effective intraocular pressure lowering dose over a period of 6 hours.

Ocular inserts, particularly preferred in the practice of the present invention, are conventionally prepared, for example, by soaking the polymeric insert or soft lens in an effective amount of a solution of the compound of Formula I or an ophthalmologically acceptable acid addition salt thereof until equilibrium is established, which is generally within a period of one to five minutes. Inserts prepared in this manner diffuse at a rate sufficient to provide a therapeutic dose to the eyeball over a period of six hours.

From the foregoing description, one of ordinary skill in the art can easily ascertain the essential characteristics of this invention, and without departing from the spirit and scope thereof, can make verious changes and/or modifications to the invention for adapting it to various usages and contitions. Accordingly, such changes and modifications are properly, equitably and intended to be, within the full range of equivalence of the following claims.

What I claim is:

1. A method for lowering intraocular pressure in a warm-blooded animal in need of such treatment which comprises topically applying to the eye thereof, an effective opthalmologically acceptable amount for lowering intraocular pressure of a compound selected from the group consisting of:

Formula I

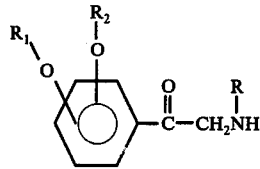

wherein R represents a memeber selected from the group consisting of hydrogen or a $C_1$-$C_5$ straight or branched alkyl group; and wherein $R_1$ and $R_2$, which may be the same or different, represents an acyl member selected from the group consisting of alkanoyl having 1-22 carbon atoms, alkenoyl having one or two douple bonds and having 4-22 carbon atoms,

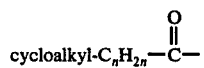

having a total of 4-10 carbon atoms of which 3-7 are ring carbon atoms in cycloalkyl and wherein $n$ is zero, one, or two, phenoxyacetyl, naphthalenecarbonyl, pyridinecarbonyl,

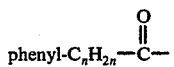

wherein $n$ is zero, one or two and phenyl is unsubstituted or is substituted by 1-3 alkyl having 1-4 carbon atoms, alkoxy having 1-4 carbon atoms, halo, trifluoromethyl, dialkylamino having 2-8 carbon atoms, and alkanoylamino having 1-6 carbon atoms; and an ophthalmologically acceptable acid addition salt thereof.

2. The method of claim 1, wherein said compound is: 3,4-Bis(pivalyloxy)phenyl-methylaminomethyl ketone hydrochloride.

3. The method of claim 1, wherein said compound is: 3,4-bis(p-toluyloxy)phenyl-methylaminomethyl-ketone hydrochloride.

4. The method of claim 1, wherein said compound is: 3,4-bis(hexanoyloxy)phenyl-methylaminomethyl-ketone hydrochloride.

5. The method of claim 1, wherein said compound is: 3,4-bis(nicotinoyloxy)phenyl-methylaminomethyl-ketone hydrochloride.

6. The method of claim 1, wherein said compound is: 3,4-bis(phenylacetyloxy)phenyl-methylaminomethyl-ketone hydrochloride.

7. The method of claim 1, wherein said compound is: 3,4-bis(pivalyloxy)phenyl-aminomethyl-ketone hydrochloride.

8. The method of claim 1, wherein said compound is: 3,4-bis(p-toluyloxy)phenyl-aminomethyl-ketone hydrochloride.

9. The method of claim 1, where said compound is: 3,4-bis(hexanoyloxy)phenyl-aminomethyl-ketone hydrochloride.

10. The method of claim 1, wherein said compound is: 3,4bis-(nicotinoyloxy)phenyl-aminomethyl-ketone hydrochloride.

11. The method of claim 1, wherein said compound is: 3,4-bis(phenylacetyloxy)phenyl-aminomethyl-ketone hydrochloride.

12. The method of claim 1, wherein said compound is: 3,4-bis(pivalyloxy)phenyl-isopropylaminomethyl-ketone hydrochloride.

13. The method of claim 1, wherein said compound is: 3,4-bis(p-toluyloxy)phenyl-isopropylaminomethyl-ketone hydrochloride.

14. The method of claim 1, wherein said compound is: 3,4-bis(hexanoyloxy)phenyl-isopropylaminomethyl-ketone hydrochloride.

15. The method of claim 1, wherein said compound is: 3,4-bis(nicotinoyloxy)phenyl-isopropylaminomethyl-ketone hydrochloride.

16. The method of claim 1, wherein said compound is: 3,4-bis(phenylacetyloxy)phenyl-isopropylaminomethyl-ketone hydrochloride.

17. The method of claim 1, wherein said compound is administered in combination with a nontoxic pharmaceutically acceptable ophthalmological carrier.

18. The method of claim 17, wherein said carrier is an isotonic aqueous sodium chloride solution.

19. The method of claim 17, wherein aid compound and carrier are contained in a polymeric ophthalmologically acceptable ocular insert.

20. The method of claim 17, wherein said compound and carrier are contained in an ophthalmologically acceptable soft, polymeric contact lens.

21. The method of claim 1, wherein said warm-blooded animal is a mammal.

* * * * *